(12) United States Patent
Sajitz et al.

(10) Patent No.: US 8,901,342 B2
(45) Date of Patent: Dec. 2, 2014

(54) METHOD FOR PRODUCING ACYLOXY BENZOIC ACIDS

(75) Inventors: Melanie Sajitz, Plettenberg (DE); Isabel Scheffer, Frankfurt am Main (DE); Werner Janitschek, Heistenbach (DE)

(73) Assignee: Clariant International Ltd, Muttenz (CH)

( * ) Notice: Subject to any disclaimer, the term of this patent is extended or adjusted under 35 U.S.C. 154(b) by 0 days.

(21) Appl. No.: 13/816,650

(22) PCT Filed: Aug. 6, 2011

(86) PCT No.: PCT/EP2011/003956
§ 371 (c)(1),
(2), (4) Date: Mar. 20, 2013

(87) PCT Pub. No.: WO2012/019742
PCT Pub. Date: Feb. 16, 2012

(65) Prior Publication Data
US 2013/0211131 A1    Aug. 15, 2013

(30) Foreign Application Priority Data
Aug. 13, 2010 (DE) .................. 10 2010 034 244

(51) Int. Cl.
*C07C 67/14* (2006.01)
*C11D 3/39* (2006.01)

(52) U.S. Cl.
CPC ............ *C07C 67/14* (2013.01); *C11D 3/391* (2013.01)
USPC ....................................................... 560/98

(58) Field of Classification Search
None
See application file for complete search history.

(56) References Cited

U.S. PATENT DOCUMENTS

| 5,380,917 A | 1/1995 | Kottwitz et al. |
| 5,891,838 A * | 4/1999 | Angell et al. .............. 510/312 |
| 2005/0230660 A1 * | 10/2005 | Parker et al. ............. 252/299.2 |

FOREIGN PATENT DOCUMENTS

| EP | 0164786 A2 | 12/1985 |
| EP | 0294073 A1 | 12/1988 |
| JP | 2000086581 | 3/2000 |
| WO | 9215556 A1 | 9/1992 |

OTHER PUBLICATIONS

Chamblee et al. Green Chemistry 2004, 6, 382-386.*

* cited by examiner

*Primary Examiner* — Brandon Fetterolf
*Assistant Examiner* — Ana Z Muresan
(74) *Attorney, Agent, or Firm* — Michael W. Ferrell

(57) ABSTRACT

The invention relates to a method for producing acyloxy benzoic acids of the formula (I), in which $R^1$ is a linear or branched saturated alkyl group with 6 to 30 carbon atoms, a linear or branched mono- or polyunsaturated alkenyl group with 6 to 30 carbon atoms, or an aryl group with 6 to 30 carbon atoms. The acyloxy benzoic acids of the formula (I) are produced from para-hydroxy benzoic acid and a corresponding carboxylic acid halogenide in the presence of a base and are advantageously suitable for use as activators for hydrogen peroxide.

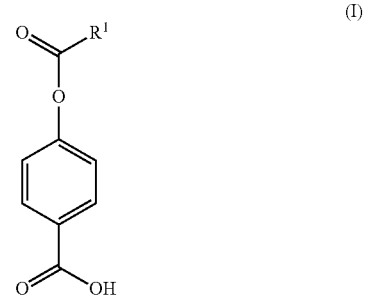

19 Claims, No Drawings

METHOD FOR PRODUCING ACYLOXY BENZOIC ACIDS

The present invention relates to a process for preparing acyloxybenzoic acids starting from para-hydroxybenzoic acid and carboxylic halides.

Inorganic peroxygen compounds, especially hydrogen peroxide and solid peroxygen compounds which dissolve in water and in so doing release hydrogen peroxide, such as sodium perborate and sodium percarbonate, have long been used as oxidizing agents for purposes of disinfection and bleaching. The oxidation effect of these substances in dilute solutions is heavily dependent on the temperature. For example, with $H_2O_2$ or perborate in alkaline bleaching liquors, sufficiently rapid bleaching of soiled textiles is obtained only at temperatures above about 80° C.

At lower temperatures, the oxidation effect of the inorganic peroxygen compounds can be improved by addition of what are called bleach activators. Numerous proposals for this have been elaborated in the past, especially from the classes of the N- or O-acyl compounds.

In recent years, the compounds according to the formula (Ia)

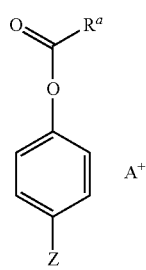

$Z = CO_2^-, SO_3^-$ in which the radical $R^a$ in particular is a linear or branched, saturated alkyl group having 6 to 22 carbon atoms or is a linear or branched, singly or multiply unsaturated alkenyl group having 6 to 22 carbon atoms, and $A^+$ in particular is an alkali metal or alkaline earth metal ion, and preferably a sodium ion, have been of interest as activators for inorganic peroxy compounds. Of particular interest was the use of these compounds as bleaching agents or as a peroxy acid precursor.

These peroxy acid precursors react in aqueous solution with the inorganic peroxy compounds such as sodium percarbonate or sodium perborate which are present in the laundry detergent, and form organic peroxy acids which bleach much more effectively at low temperatures (<70° C.) than do the inorganic peroxy compounds.

Of particular note are acyloxybenzoic acids according to the formula (Ib)

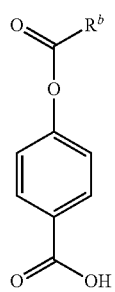

in which $R^b$ in particular is a linear or branched, saturated alkyl group having 6 to 30 carbon atoms, a linear or branched, singly or multiply unsaturated alkenyl group having 6 to 30 carbon atoms, or an aryl group having 6 to 30 carbon atoms, and also the salts thereof, these being, in particular, alkali metal salts or alkaline earth metal salts, since not only are they very good bleach activators, but they are also found, advantageously, not to be skin-sensitizing.

Not only the phenol ester sulfonates but also the acyloxybenzoic acids and salts thereof are obtainable in principle, for example, through reaction of carboxylic chlorides such as, for example, alkyl acid chloride with phenol-sulfonate or para-hydroxybenzoic acid by the Schotten-Baumann reaction. Examples of this are found inter alia in EP 0 294 073, EP 0 164 786, or WO 92/15556.

The acyloxybenzoic acids can be prepared from acid chlorides and para-hydroxybenzoic acid even at high temperatures >30° C. (JP 4194688). A disadvantage of the process, however, is the formation of secondary components such as dimers and trimers of the para-hydroxybenzoic acid and/or esters of the dimeric para-hydroxybenzoic acid. The incidence of such secondary components, which cannot be separated off, is extremely undesirable in laundry detergents.

U.S. Pat. No. 5,891,838 discloses a process for preparing para-decanoyloxybenzoic acid that provides diethyl ether and water as a solvent mixture. The yield of 40%, however, is unsatisfactory, and the industrial handling of diethyl ether is undesirable on workplace safety grounds.

It was an object of the present invention to provide a process for preparing long-chain or aromatic acyloxybenzoic acids that can be carried out on an industrial scale and leads in high yields to the acyloxybenzoic acids, the acyloxybenzoic acids being suitable, in terms of composition and quality, for use in laundry and other detergents.

It has now been found that this object is achieved by a process for preparing acyloxybenzoic acids of the formula (I)

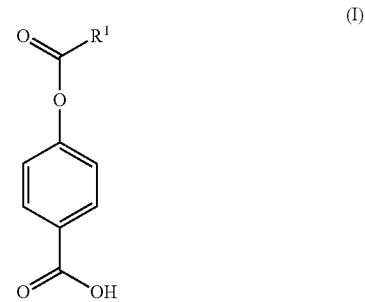

in which
$R^1$ is a linear or branched, saturated alkyl group having 6 to 30 carbon atoms, a linear or branched, singly or multiply unsaturated alkenyl group having 6 to 30 carbon atoms, or an aryl group having 6 to 30 carbon atoms, which is characterized in that
a) a carboxylic halide of the formula $R^1COHal$, in which $R^1$ possesses the definition indicated above and Hal is a halide, is reacted with para-hydroxybenzoic acid in the presence of base in a solvent mixture comprising water and one or more organic solvents at a temperature ≤25° C. and a pH of 9 to 11.5,
b) the reaction mixture after step a), at a temperature ≤25° C., is adjusted to a pH of 6 to 8 by addition of acid, and
c) the reaction mixture after step b) is heated to a temperature of 35 to 80° C. and thereafter adjusted to a pH of 1 to 4 by addition of acid.

The invention accordingly provides a process for preparing acyloxybenzoic acids of the formula (I)

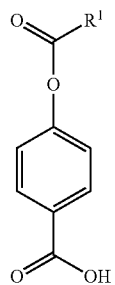
(I)

in which
R¹ is a linear or branched, saturated alkyl group having 6 to 30, preferably 7 to 15 and more preferably 7 to 11 carbon atoms, a linear or branched, singly or multiply unsaturated alkenyl group having 6 to 30, preferably 7 to 15 and more preferably 7 to 11 carbon atoms, or an aryl group having 6 to 30 carbon atoms, characterized in that
a) a carboxylic halide of the formula R¹COHal, in which R¹ possesses the definition indicated above and Hal is a halide, is reacted with para-hydroxybenzoic acid in the presence of base in a solvent mixture comprising water and one or more organic solvents at a temperature ≤25° C. and preferably from 0 to 25° C. and at a pH of 9 to 11.5, preferably of 10 to 11 and more preferably of 10.3 to 10.7,
b) the reaction mixture after step a), at a temperature ≤25° C. and preferably of 0 to 25° C., is adjusted to a pH of 6 to 8 by addition of acid, and
c) the reaction mixture after step b) is heated to a temperature of 35 to 80° C., preferably of 50 to 75° C., and thereafter adjusted to a pH of 1 to 4 by addition of acid, preferably HCl.

The process of the invention affords the advantage that the acyloxybenzoic acids of the formula (I) can be easily isolated from the reaction mixture by filtration. The acyloxybenzoic acids obtained by the process of the invention are white to cream in color and can be used in the form of powder or granules for the manufacture of laundry and other detergents. A particular advantage is that the acyloxybenzoic acids obtained by the process of the invention have a very high purity and contain secondary components such as dimers or trimers of the para-hydroxybenzoic acid preferably in an amount <1.0% by weight, more preferably in an amount <0.3% by weight, and with more particular preference in an amount <0.1% by weight. In contrast to acyloxybenzoic acids from other processes, which generally contain byproducts, the acyloxybenzoic acids from the process of the invention, on account of their high purity, are especially suitable for use in laundry and other detergents.

In the process of the invention, it is not the entire amount of the base used in step a) that is added to the reaction mixture before the carboxylic halide is added. Instead, in the course of step a), the base is metered in at a rate such that during the conversion or reaction of the carboxylic halide with the phenolate originating from para-hydroxybenzoic acid, the pH in step a) is held within the pH range from 9 to 11.5, preferably from 10 to 11, and more preferably from 10.3 to 10.7.

The procedure in step a) of the process of the invention is preferably such that the carboxylic halide of the formula R¹COHal is added to a mixture of para-hydroxybenzoic acid and base in a solvent mixture comprising water, and the one or more organic solvents are added. In this case, initially, however, the amount of base added to the reaction mixture is only such as to achieve an initial pH of 9 to 11.5, preferably of 10 to 11, and more preferably of 10.3 to 10.7. Since hydrogen halide HHal, where Hal possesses the definition indicated above, is formed in the course of the reaction in step a), the pH of the reaction mixture is lowered in the course of reaction. By addition of further base, the pH throughout step a) is held within the abovementioned range of 9 to 11.5, preferably of 10 to 11, and more preferably of 10.3 to 10.7.

Preferred carboxylic halides of formula R¹COHal are those in which Hal is Cl, Br or I. Particularly preferred carboxylic halides of the formula R¹COHal are those in which Hal is Cl or Br. Especially preferred carboxylic halides of the formula R¹COHal are the carboxylic chlorides according to the formula (II)

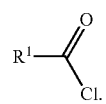
(II)

Where the radical R¹ represents an aryl group, it is preferably a phenyl group or else a phenyl group substituted by 1 to 3 methyl groups. Among these substituted phenyl groups, the group —C₄H₆—CH₃ is preferred in turn. Among the aryl groups, however, the (unsubstituted) phenyl group is particularly preferred.

Preferably, though, the radical R¹ is an alkyl or alkenyl group. Examples of carboxylic acids R¹—COOH which form the basis for the carboxylic halides R¹—COHal are heptanoic acid, octanoic acid, methyloctanoic acid, nonanoic acid, 3,3,5-isononanoic acid, decanoic acid, undecanoic acid, undecenoic acid, dodecanoic acid, tetradecanoic acid, hydrogenated tallow fatty acid, and octadecanoic acid.

More preferably the radical R¹ is an alkyl group. With more particular preference, the carboxylic acids R¹—COOH on which the carboxylic halides are based are selected from the group consisting of octanoic acid, nonanoic acid, 3,3,5-isononanoic acid, decanoic acid and dodecanoic acid. Among these, nonanoic acid and decanoic acid are preferred in turn, and decanoic acid is particularly preferred.

The process of the invention is preferably performed such that after step c) the reaction mixture is cooled to a temperature <35° C., more preferably <30° C., with more particular preference from 0 to 30° C., and extraordinarily preferably from 5 to 25° C. (step d)). In this way it is possible in particular to achieve a boost in yield.

The acyloxybenzoic acids of the formula (I) prepared by the process of the invention are preferably in the form of particles having $d_{50}$ values of 10 to 150 μm. Among these particles, preference in turn is given to those which possess $d_{10}$ values of 5 to 30 μm and $d_{90}$ values of 30 to 200 μm.

The acyloxybenzoic acids of the formula (I) that are prepared by the process of the invention are more preferably in the form of particles having $d_{50}$ values of 12 to 100 μm. Among these particles, preference is given in turn to those which possess $d_{10}$ values of 6 to 25 μm and $d_{90}$ values of 40 to 150 μm.

In the context of the present specification, the $d_{50}$ values of the particles produced by the process of the invention are defined as follows: a $d_{50}$ value of "x" μm means that exactly 50% by volume of the particles possess a diameter of less than "x" µm. The analogous definition applies in respect of the $d_{10}$ and $d_{90}$ values as well.

The reported $d_{10}$, $d_{50}$, and $d_{90}$ values are values for the acyloxybenzoic acids of the formula (I) prepared by the process of the invention, without subsequent treatment such as sieving or grinding, for example; in other words, they represent values for acyloxybenzoic acids of the formula (I) that are obtained directly from the process of the invention.

The measurement of the particle sizes of the acyloxybenzoic acids of the formula (I) that are prepared by the process of the invention, and also of their $d_{10}$, $d_{50}$, and $d_{90}$ values, takes place by the method of laser diffraction. The instrument used was a Mastersizer 2000 with a Scirocco 2000 dispersing unit, from the company Malvern Instruments. The Scirocco 2000 dispersing unit operates on the basis of air pressure. Measurement took place at room temperature (25° C.) using 2 g of the sample. Evaluation was made via the Fraunhofer theory (general purpose model).

The function of the base added during the acylation reaction in step a) of the process of the invention is to allow the reaction, by formation of the phenolate, and to bind the liberated hydrogen halide HHal in the form of salt. Suitable bases are in principle all those which are strong enough to form the phenolate from the para-hydroxybenzoic acid. The base used in step a) of the process of the invention is preferably selected from alkali metal hydroxides. With particular preference, the base used in step a) of the process of the invention is KOH or NaOH.

The one or more organic solvents used in step a) of the process of the invention are preferably selected from the group consisting of linear or branched alcohols and open-chain or cyclic ethers.

More preferably, the one or more organic solvents used in step a) of the process of the invention possess from 1 to 10 carbon atoms and preferably from 1 to 6 carbon atoms.

In one especially preferred embodiment of the invention, the alcohols used as organic solvents are selected from secondary and tertiary alcohols having 3 to 6 carbon atoms.

In another especially preferred embodiment of the invention, the one or more organic solvents used in step a) of the process of the invention possess from 1 to 5 carbon atoms. Of these, in turn, preference is given to the one or more organic solvents used in step a) being selected from the group consisting of methanol, ethanol, n-propanol, isopropanol, n-butanol, isobutanol, tert-butanol, diethyl ether, tetrahydrofuran, dioxane, and mixtures thereof.

Very preferably the organic solvent used in step a) of the process of the invention is isopropanol.

The acid used in steps b) and c) of the process of the invention preferably possesses a pKa value of less than or equal to 4.0. This acid more preferably is $H_2SO_4$ or HCl, and especially preferably HCl.

The weight ratio of water to the one or more organic solvents in step a) is preferably from 5:1 to 1:5 and more preferably from 3:1 to 1:2.

The weight ratio of water to para-hydroxybenzoic acid in step a) is preferably from 2:1 to 10:1 and more preferably from 2:1 to 6:1.

The molar ratio of the carboxylic halide of the formula $R^1$COHal to the para-hydroxybenzoic acid is preferably from 0.75:1 to 1.5:1, more preferably from 0.9:1 to 1.1:1, and especially preferably 1:1.

The molar ratio of base which is used in step a) of the process of the invention to para-hydroxybenzoic acid is preferably from 2:1 to 2.5:1. The amounts of base indicated here constitute the total amount of base used in step a) of the process of the invention.

The procedure for isolating and purifying the acyloxybenzoic acids of the formula (I) that are prepared by the process of the invention is preferably as follows: The reaction mixture is filtered by conventional separation methods (filter apparatus), preferably at room temperature, and the residue is washed with water until there is no longer any salt present. Filtration takes place preferably after step d). The acyloxybenzoic acid formed is obtained in high yields in the form of a white powder, which can be dried by conventional methods.

The end product contains traces at most of the carboxylic acid $R^1$—COOH. Unreacted para-hydroxybenzoic acid and salts such as sodium chloride, for example, can be removed completely from the filter cake by washing with water.

The present invention further provides an acyloxybenzoic acid obtainable by the process of the invention.

The product of the process of the invention can be used advantageously as an activator for hydrogen peroxide.

The present invention accordingly further provides the use of an acyloxybenzoic acid obtainable by the process of the invention as an activator for hydrogen peroxide.

In their action as bleach activators, the acyloxybenzoic acids obtainable by the process of the invention are significantly more effective than acyloxybenzoic acids prepared by conventional processes. With the acyloxybenzoic acids obtainable by the process of the invention, the release of peracid takes place significantly earlier than in the case of acyloxybenzoic acids prepared by conventional processes.

The acyloxybenzoic acids obtainable by the process of the invention can be used as persalt activators in liquid or powder laundry and other detergents such as heavy-duty laundry powder detergents, scouring salts, or machine powder dishwash detergents. In order to increase the shelf life in these formulations, the acids may be converted into a granular form, as known to the skilled person. As a result of the activation, it is possible, in laundry and other detergents, for example, to enhance the bleaching performance of the inorganic peroxy compounds/hydrogen peroxide or, in disinfectants, to boost the disinfection performance.

The examples below are intended to illustrate the invention, though without confining it to them.

EXAMPLES

Example 1

Synthesis of Para-Decanoyloxybenzoic Acid (DOBA)

69.1 g (0.5 mol) of para-hydroxybenzoic acid were first dissolved in 200 ml of water and 300 ml of isopropanol and this solution was adjusted to a pH of 10.5 at 20 to 25° C. using 87.4 g of NaOH solution (32% strength by weight aqueous solution, 0.7 mol). Metered in to this solution at a pH of 10.5 subsequently, over the course of three hours, were 95.4 g (0.5 mol) of decanoyl chloride. The pH was held at 10.5 using 40.5 g of NaOH solution (32% strength by weight aqueous solution, 0.324 mol) and the temperature was held at 20 to 25° C. The batch was stirred for one hour thereafter. Subsequently the reaction mixture was adjusted to a pH of 7 at 20 to 25° C. using 5.3 g of HCl solution (32% strength by weight aqueous solution), and the complete solution was heated to 65 to 70° C. and then adjusted to a pH of 1.5 to 3 using 60 g of HCl solution (32% strength by weight aqueous solution). The reaction mixture was cooled to room temperature (25° C.), and the solid was filtered off on a suction filter and washed ten times with 150 ml of water. The yield after drying under reduced pressure at 100° C. was 134.1 g (91.7% of theory). According to HPLC and NMR measurement, the product was free from decanoic acid and from unreacted para-hydroxybenzoic acid. The purity of the product is >99.9% by weight.

Comparative Example 1

Synthesis of Para-Decanoyloxybenzoic Acid (DOBA)

69.1 g (0.5 mol) of para-hydroxybenzoic acid were first dissolved in 200 ml of water and 300 ml of isopropanol and this solution was adjusted to a pH of 10.5 at 20 to 25° C. using 87.4 g of NaOH solution (32% strength by weight aqueous solution, 0.7 mol). Metered in to this solution at a pH of 10.5 subsequently, over the course of three hours, were 95.4 g (0.5 mol) of decanoyl chloride. The pH was held at 10.5 using 40.5 g of NaOH solution (32% strength by weight aqueous solution, 0.324 mol) and the temperature was held at 20 to 25° C. The batch was stirred for one hour thereafter. Subsequently the reaction mixture was adjusted to a pH of 1.5 to 3 at 20 to 25° C. using 65.3 g of HCl solution (32% strength by weight aqueous solution). The reaction mixture was filtered on a suction filter. Here there were considerable problems, since the suction filter/filtration unit clogged up, owing to the size of the product crystals. The experiment had to be terminated at this point. The same occurs if the product is precipitated at 65° C. and the reaction mixture is filtered at 35 to 65° C.

Example 2

Synthesis of Para-Decanoyloxybenzoic Acid (DOBA)

The process was as in example 1, but the solvent mixture was used in the converse proportion. 300 ml of water and 200 ml of isopropanol were used as the solvent mixture. The yield was 127.2 g (87.0% of theory). The purity of the product is >99.9% by weight.

Example 3

Synthesis of Para-Decanoyloxybenzoic Acid (DOBA)

The process was as in example 1, but at a batch size of 0.5 mol the temperature was held at 0 to 5° C. during the metering of the decanoyl chloride and during the subsequent stirring, and also during the addition of HCl solution in accordance with step b) of the process of the invention. The yield was 133.9 g (91.6% of theory). The purity of the product is >99.9% by weight.

Example 4

Synthesis of Para-Benzoyloxybenzoic Acid (BOBA)

69.1 g (0.5 mol) of para-hydroxybenzoic acid were first dissolved in 200 ml of water and 300 ml of isopropanol and this solution was adjusted to a pH of 10.5 at 20 to 25° C. using 87.4 g of NaOH solution (32% strength by weight aqueous solution, 0.7 mol). Metered into this solution then at a pH of 10.5, over the course of three hours, were 70.2 g (0.5 mol) of benzoyl chloride. The pH was held at 10.5 using 40.5 g of NaOH solution (32% strength by weight aqueous solution, 0.324 mol), and the temperature was held at 20 to 25° C. The batch was stirred for one hour thereafter. Subsequently the reaction mixture was adjusted to a pH of 7 at 20 to 25° C. using 5.3 g of HCl solution (32% strength by weight aqueous solution) and adjusted to a pH of 1.5 to 3 at 65 to 70° C. using 60 g of HCl solution (32% strength by weight aqueous solution). The reaction mixture was cooled to room temperature (25° C.) and the solid was filtered off on a suction filter and washed ten times with 150 ml of water. The yield after drying under reduced pressure at 100° C. was 119.1 g (98.3% of theory). According to HPLC and NMR measurement, the product was free from benzoic acid and from unreacted para-hydroxybenzoic acid. The purity of the product is >99.9% by weight.

Example 5

Synthesis of Para-Nonanoyloxybenzoic Acid (NOBA)

69.1 g (0.5 mol) of para-hydroxybenzoic acid were first dissolved in 200 ml of water and 300 ml of isopropanol and this solution was adjusted to a pH of 10.5 at 20 to 25° C. using 87.4 g of NaOH solution (32% strength by weight aqueous solution, 0.7 mol). Metered into this solution then at a pH of 10.5, over the course of three hours, were 88.3 g (0.5 mol) of nonanoyl chloride. The pH was held at 10.5 using 40.5 g of NaOH solution (32% strength by weight aqueous solution, 0.324 mol), and the temperature was held at 20 to 25° C. The batch was stirred for one hour thereafter. Subsequently the reaction mixture was adjusted to a pH of 7 at 20 to 25° C. using 5.3 g of HCl solution (32% strength by weight aqueous solution) and adjusted to a pH of 1.5 to 3 at 65 to 70° C. using 60 g of HCl solution (32% strength by weight aqueous solution). The reaction mixture was cooled to room temperature (25° C.) and the solid was filtered off on a suction filter and washed ten times with 150 ml of water. The yield after drying under reduced pressure at 100° C. was 121.3 g (87.2% of theory). According to HPLC and NMR measurement, the product was free from nonanoic acid and from unreacted para-hydroxybenzoic acid. The purity of the product is >99.9% by weight.

Example 6

Synthesis of Para-Decanoyloxybenzoic Acid (DOBA)

69.1 g (0.5 mol) of para-hydroxybenzoic acid were first dissolved in 200 ml of water and 300 ml of isopropanol and this solution was adjusted to a pH of 10.5 at 20 to 25° C. using 78.4 g of KOH solution (50% strength by weight aqueous solution, 0.7 mol). Metered into this solution then at a pH of 10.5, over the course of three hours, were 95.4 g (0.5 mol) of decanoyl chloride. The pH was held at 10.5 using 44.0 g of KOH solution (50% strength by weight aqueous solution, 0.392 mol), and the temperature was held at 20 to 25° C. The batch was stirred for one hour thereafter. Subsequently the reaction mixture was adjusted to a pH of 8 at 20 to 25° C. using 10 g of HCl solution (32% strength by weight aqueous solution) and adjusted to a pH of 1.5 to 3 at 65 to 70° C. using 55 g of HCl solution (32% strength by weight aqueous solution). The reaction mixture was cooled to room temperature (25° C.) and the solid was filtered off on a suction filter and washed ten times with 150 ml of water. The yield after drying under reduced pressure at 100° C. was 131.5 g (90.0% of theory). According to HPLC and NMR measurement, the product was free from decanoic acid and from unreacted para-hydroxybenzoic acid. The purity of the product is >99.9% by weight.

Example 7

Synthesis of Para-Decanoyloxybenzoic Acid (DOBA)

The process was as in example 6, but the metering of the decanoyl chloride, the subsequent stirring and the addition of the HCl solution in accordance with step b) of the process of the invention were carried out at 10 to 15° C. The yield was 133.2 g (91.0% of theory). The purity of the product is >99.9% by weight.

Comparative Example 2

Synthesis of Para-Decanoyloxybenzoic Acid (DOBA)

116.3 g (0.61 mol) of decanoyl chloride were heated in 300 ml of xylene to 125° C. and over the course of 6 hours 69.1 g (0.5 mol) of 4-hydroxybenzoic acid were introduced in portions. The batch was stirred at 125° C. for 1 hour thereafter, cooled to room temperature, and filtered with suction, and the filter product was washed three times with 45 ml of xylene. The yield after drying under reduced pressure at 100° C. was 108.4 g (74% of theory). According to HPLC and NMR measurement, the product was free from decanoic acid and from unreacted para-hydroxybenzoic acid, but contained 0.4% by weight of byproducts such as dimers and trimers of the para-hydroxybenzoic acid.

Comparative Example 3

Synthesis of Para-Decanoyloxybenzoic Acid (DOBA) According to U.S. Pat. No. 5,891,838, Example XV DOBA was prepared according to example XV of U.S. Pat. No. 5,891,838. After the filtration of the product (which had a greasy consistency, with the disadvantageous consequence of making the filtration last a very long time), the work-up procedure was as follows: the residue from the filtration was washed with water a number of times, and the product was dried under reduced pressure at 100° C. The yield was 90.6 g. According to HPLC and NMR measurement, the product contained 10.9% by weight of decanoic acid, 30.4% by weight of DOBA, and 41% by weight of para-hydroxybenzoic acid. The product was subsequently recrystallized for purification, as in U.S. Pat. No. 5,891,838, and employed for the measurement of the peracid kinetics (see example 8 below).

Example 8

Determining the Peracid Kinetics of Para-Decanoyloxybenzoic Acid (DOBA) from Inventive Example 1 and from Comparative Examples 2 and 3

The peracid kinetics were determined by means of iodometric titration using sodium thiosulfate solution.

The basis for the measurement is that para-decanoyloxybenzoic acid (DOBA) and hydrogen peroxide react in aqueous solution to form perdecanoic acid and para-hydroxybenzoic acid (if inorganic peroxides are used, they react in aqueous solution to form hydrogen peroxide). The reaction between DOBA and hydrogen peroxide takes place rapidly and quantitatively in dilute aqueous solution at a pH of 10 to 11 and at 20° C. The perdecanoic acid formed can then be determined by iodometry, along with the hydrogen peroxide which is present in excess. The perdecanoic acid is substantially more reactive than hydrogen peroxide and, in a weakly acidic medium and at a low temperature, it undergoes immediate oxidation with added iodide $I^-$ (added in the form of potassium iodide, for example) to form iodine $I_2$. The iodine formed can then be titrated with sodium thiosulfate. The corresponding amount of perdecanoic acid can then be calculated from the amount of iodine found.

The specific procedure was as follows:

1 liter of deionized water at 20° C. was introduced in a 2 liter glass beaker and stirred. 1.5 g of sodium percarbonate and 8 g of a standard laundry detergent ("IEC 60 456 Type A*" from WFK Testgewebe GmbH) were added and subjected to preliminary dissolution for 2 minutes. Then 0.25 g of the DOBA under analysis was added. After 3 minutes, 50 ml were pipetted off and introduced into a 250 ml glass beaker, onto 50 g of ice made from deionized water and 10 ml of acetic acid (20% strength by weight aqueous solution). Then 5 ml of aqueous potassium iodide solution (10% strength by weight aqueous solution) were added, and titration took place with sodium thiosulfate solution (0.01 molar aqueous solution).

Titration was carried out using a Titrino DMS 716 or Basic 794 (metrohm) with a 50-way changeover unit and keyboard, and also a Ti Stand 727 (metrohm) with drawn burette tip, stirring rod, and combined platinum electrode.

The next samples were taken after particular times following the addition of DOBA, and were titrated as described above. As sampling time goes on, the amount of perdecanoic acid approaches a maximum value, and then remains constant in the case of samples taken later. This maximum value for the amount of perdecanoic acid is set at 100%. The amounts of perdecanoic acid for the other samples are then expressed in relation to this 100%.

The results for the determination of the peracid kinetics, i.e., the results of determination of the amount of perdecanoic acid as a function of time, are shown in table 1.

TABLE 1

Results of the determination of peracid kinetics of para-decanoyloxybenzoic acid (DOBA)

| | Amount of perdecanoic acid [%] | | |
|---|---|---|---|
| Time [min.] | Using DOBA from inventive example 1 | Using DOBA from comparative example 2 | Using DOBA from comparative example 3 |
| 3 | 89.83 | 66.85 | 82.04 |
| 6 | 96.39 | 82.92 | 84.28 |
| 9 | 98.53 | 87.98 | 88.00 |
| 12 | 100.00 | 92.91 | 93.38 |
| 15 | | 96.44 | 94.32 |
| 18 | | 100.00 | 100.00 |

The results in table 1 describe the release of active ingredient from para-decanoyloxybenzoic acid (DOBA), i.e., here, the release of perdecanoic acid, as a function of time. They reveal that the active ingredient is released more quickly from the DOBA produced according to inventive example 1 than is the active ingredient from the DOBAs produced according to comparative examples 2 and 3. Specifically, it is apparent from the results from table 1 that the DOBA produced by comparative examples 2 and 3 has generated 100% of the perdecanoic acid only after 18 minutes, whereas the DOBA produced by inventive example 1 reaches this level after just 12 minutes.

With a view to the use of the resultant acyloxybenzoic acids of the formula (I) in laundry detergents, therefore, the process of the invention represents a significant improvement.

Example 9

Synthesis of Para-Decanoyloxybenzoic Acid (DOBA)

The process was as in example 1, but at a batch size of 4500 mol the temperature was held at 10 to 15° C. during the metering of the decanoyl chloride and during the subsequent stirring, and also during the addition of HCl solution in accordance with step b) of the process of the invention. The purity of the product is >99.9% by weight. The $d_{10}$ value of the particles is 14.833 µm, the $d_{50}$ value is 54.757 µm, and the $d_{90}$ value is 111.505 µm.

The invention claimed is:

1. A process for preparing an acyloxybenzoic acid of the formula (I)

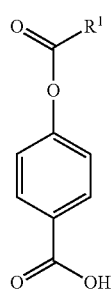

(I)

in which
R$^1$ is a linear or branched, saturated alkyl group having 6 to 30 carbon atoms, a linear or branched, singly or multiply unsaturated alkenyl group having 6 to 30 carbon atoms, or an aryl group having 6 to 30 carbon atoms,
comprising the steps of
a) reacting a carboxylic halide of the formula R$^1$COHal, in which R$^1$ is defined above and Hal is a halide, with para-hydroxybenzoic acid in the presence of base, wherein the base is selected from alkali metal hydroxides, in a solvent mixture comprising water and at least one organic solvent, wherein the organic solvent is isopropanol, at a temperature ≤25° C. and a pH of 9 to 11.5,
b) adjusting the pH of the reaction mixture after step a), at a temperature ≤25° C., to a pH of 6 to 8 by addition of acid, and
c) subsequently heating the reaction mixture after step b) to a temperature of 35 to 80° C. and thereafter adjusting the pH of the reaction mixture to a pH of 1 to 4 by addition of acid.

2. The process as claimed in claim 1, wherein after step c) the reaction mixture is cooled to a temperature <35° C.

3. The process as claimed in claim 1 wherein the acyloxybenzoic acids of the formula (I) are present in the form of particles having $d_{50}$ values of 10 to 150 µm.

4. The process as claimed in claim 3, wherein the particles have $d_{10}$ values of 5 to 30 µm and $d_{90}$ values of 30 to 200 µm.

5. The process as claimed in claim 1, the base in step a) is KOH or NaOH.

6. The process as claimed in claim 1, the acid in steps b) and c) has a pKa value of less than or equal to 4.0.

7. The process as claimed in claim 1, the acid in steps b) and c) is $H_2SO_4$ or HCl.

8. The process as claimed in claim 1, wherein the weight ratio of water to the at least one organic solvent in step a) is from 5:1 to 1:5.

9. The process as claimed in claim 1, wherein the weight ratio of water to para-hydroxybenzoic acid in step a) is from 2:1 to 10:1.

10. The process as claimed in claim 1, wherein R$^1$ is a linear or branched, saturated alkyl group having 6 to 30 carbon atoms, or a linear or branched, singly or multiply unsaturated alkenyl group having 6 to 30 carbon atoms.

11. The process as claimed in claim 10, wherein the radical R$^1$ is an alkyl group.

12. The process as claimed in claim 10, wherein a carboxylic acid, R$^1$—COOH from which the carboxylic halide R$^1$—COHal is derived is selected from the group consisting of octanoic acid, nonanoic acid, 3,3,5-isononanoic acid, decanoic acid and dodecanoic acid.

13. The process as claimed in claim 12, wherein the carboxylic acid from which the carboxylic halide R$^1$—COHal is derived is decanoic acid.

14. The process as claimed in claim 1, wherein the amount of dimers and trimers of para-hydroxybenzoic acid present in the acyloxybenzoic acid produced is less than 0.3% by weight.

15. The process as claimed in claim 14, wherein the amount of dimers and trimers of para-hydroxybenzoic acid present in the acyloxybenzoic acid produced is less than 0.1% by weight.

16. The process as claimed in claim 1, wherein the acyloxybenzoic acid produced is free from unreacted para-hydroxybenzoic acid.

17. The process as claimed in claim 1, wherein the acyloxybenzoic acid produced is free from acid of the formula R$^1$COOH.

18. The process as claimed in claim 1, wherein the acyloxybenzoic acids of the formula (I) are present in the form of particles having $d_{50}$ values of 10 to 150 µm, obtained directly from the process without subsequent treatment.

19. The process as claimed in claim 18, wherein the particles have $d_{10}$ values of 5 to 30 µm and $d_{90}$ values of 30 to 200 µm, obtained directly from the process without subsequent treatment.

* * * * *